(12) United States Patent
Ersue et al.

(10) Patent No.: US 8,059,151 B2
(45) Date of Patent: Nov. 15, 2011

(54) METHOD FOR PLANNING AN INSPECTION PATH FOR DETERMINING AREAS THAT ARE TO BE INSPECTED

(75) Inventors: Enis Ersue, Darmstadt (DE); Stephan Wienand, Zwingenberg (DE)

(73) Assignee: Isra Vision System AG, Darmstadt (DE)

( * ) Notice: Subject to any disclaimer, the term of this patent is extended or adjusted under 35 U.S.C. 154(b) by 1498 days.

(21) Appl. No.: 10/587,638

(22) PCT Filed: Feb. 10, 2005

(86) PCT No.: PCT/EP2005/001311
§ 371 (c)(1), (2), (4) Date: Jul. 28, 2006

(87) PCT Pub. No.: WO2005/090951
PCT Pub. Date: Sep. 29, 2005

(65) Prior Publication Data
US 2007/0122026 A1   May 31, 2007

(30) Foreign Application Priority Data

Feb. 18, 2004   (DE) .......................... 10 2004 007 829

(51) Int. Cl.
| | |
|---|---|
| H04N 7/18 | (2006.01) |
| G06K 9/00 | (2006.01) |
| G06K 9/46 | (2006.01) |
| G06T 15/30 | (2011.01) |
| G06F 17/50 | (2006.01) |
| G06F 19/00 | (2011.01) |
| G05B 15/00 | (2006.01) |

(52) U.S. Cl. .......... 348/86; 382/154; 382/195; 345/423; 703/1; 700/186; 700/259

(58) Field of Classification Search ..................... 348/86
See application file for complete search history.

(56) References Cited

U.S. PATENT DOCUMENTS 4,970,666 A * 11/1990 Welsh et al. .................. 345/423
5,379,347 A    1/1995 Kato et al.
(Continued)

FOREIGN PATENT DOCUMENTS

DE     197 39 250     3/1998
(Continued)

*Primary Examiner* — Christopher S Kelley
*Assistant Examiner* — Hee-Yong Kim
(74) *Attorney, Agent, or Firm* — Michael J. Striker

(57) ABSTRACT

The invention relates to a method for planning an inspection path (2) for at least one optical picture-taking device (4), particularly a camera, for inspecting a three-dimensional object (3). The picture-taking device (4) and the object (3) are movable relative to each other by means of a displacement device (5, 6). To ensure that the method for planning inspection paths and for determining areas to be inspected is easy to use and reliably covers all areas to be inspected, it is provided that, based on the design data (8), particularly CAD data and/or data determined by a sensor, relating to the object (3) and/or an area (12) to be inspected on the object, and based on the optical imaging characteristics of the picture-taking device (4), stored in electronic form, and using an arithmetic logic unit (10), the inspection path (2) for the optical picture-taking device (4) is automatically determined by specifying a specific geometric relationship between the picture-taking device (4) and the surface to be inspected.

13 Claims, 2 Drawing Sheets

U.S. PATENT DOCUMENTS

| | | | |
|---|---|---|---|
| 5,438,525 A | 8/1995 | Shimbara | |
| 5,477,268 A | 12/1995 | Shimbara et al. | |
| 5,706,408 A * | 1/1998 | Pryor | 700/259 |
| 5,715,167 A * | 2/1998 | Gupta et al. | 700/186 |
| 6,064,759 A * | 5/2000 | Buckley et al. | 382/154 |
| 6,167,151 A * | 12/2000 | Albeck et al. | 382/154 |
| 6,393,141 B1 | 5/2002 | Cronshaw et al. | |
| 2002/0141645 A1* | 10/2002 | Rajagopal et al. | 382/195 |
| 2002/0169586 A1* | 11/2002 | Rankin et al. | 703/1 |

FOREIGN PATENT DOCUMENTS

| | | |
|---|---|---|
| DE | 699 15 655 | 8/2004 |
| JP | 5080836 | 4/1993 |
| WO | 87/00629 | 1/1987 |
| WO | 00/16038 | 3/2000 |
| WO | 00/63681 | 10/2000 |

* cited by examiner

METHOD FOR PLANNING AN INSPECTION PATH FOR DETERMINING AREAS THAT ARE TO BE INSPECTED

The present invention relates to a method for planning an inspection path for at least one optical picture-taking device, particularly a camera, to inspect a three-dimensional object, with which the picture-taking device and the object are movable relative to each other using a displacement device. The present invention also relates to a method for determining areas to be inspected on a surface of a three-dimensional object based on electronically stored design data, particularly CAD data, relating to the object.

Methods exist for examining surfaces using cameras, with which a camera is moved relative to an object to be examined, and the surface of the object is scanned optically. With larger objects, it is necessary to specify an inspection path on which the optical picture-taking device or camera is moved along the object. To this end, the object to be inspected and/or the optical picture-taking device is mounted on a displacement device, e.g., a conveyor belt, a robot, a manipulator, a handling device or the like, so that the object and the picture-taking device can be moved relative to each other in, at best, all degrees of freedom. The motion sequence of this displacement device, i.e., the inspection path for the optical picture-taking device, must be specified to the control of the displacement device. This is a complex procedure when complicated, three-dimensional objects are involved, e.g., bodies, since many adjustments are required in order to scan the entire surface area of the object. Typically, the motion sequences of the displacement device must be configured manually, or they must at least be manually inspected and corrected, if necessary. To do this, the areas to be inspected on the surface of the object must also be selected. These specifications are also carried out largely manually.

The object of the present invention, therefore, is to provide methods for planning inspection paths and determining areas to be inspected that are easier to handle and that reliably cover all areas to be inspected.

This object is essentially attained with a method for planning an inspection path of the type described initially, in the following manner: Based on the design data, particularly CAD data and/or data determined by a sensor, relating to the object and/or an area to be inspected on the object, and based on the optical imaging characteristics of the picture-taking device, stored in electronic form, and using an arithmetic logic unit, the inspection path for the optical picture-taking device is automatically determined by specifying a specific geometric relationship between the picture-taking device and the surface to be inspected. It is then possible to automatically calculate the path required for the picture-taking device based on the design data and the imaging properties of the optical picture-taking device without their having to be manually calculated or determined, which is complex. By specifying certain picture-taking conditions defined in particular by specific geometric relationships between the picture-taking device and the surface to be inspected, it is possible to determine all positions for the picture-taking device, in order to completely cover the entire object or the areas to be inspected on the object during the optical inspection.

The exact form of the object to be inspected is known at any level of accuracy based on electronically-stored design data related to the object. Based on this information, an inspection path can therefore be determined automatically, without the need to manually specify the motion sequence. It is also possible, in particular, to create the relevant design data based on sensor data, e.g., by taking pictures and evaluating them, via scanning or the like. In this case, it is possible for the necessary design data related to the object to be learned automatically, rendering it unnecessary to specify them separately. The data are then stored automatically. The determination of the design data from the sensor data can be used to improve the accuracy of existing design data or to improve their resolution.

The inspection path can be planned such that the optical picture-taking device is guided over the stationary or moving object, with the possible displacements of the displacement device preferably being taken into consideration. Particularly advantageously, the displacement device can be designed as a manipulator, a handling device or a multiaxial traveling unit that permits, in particular, a motion in several degrees of freedom, e.g., around several different axes of rotation.

When planning the inspection path, picture-taking positions of the picture-taking device are preferably determined by covering the entire three-dimensional object or all areas to be inspected on the object using pictures that were taken. To this end, a check is carried out to determine whether the surfaces—determined based on the design data—of the object to be inspected are completely covered by the pictures taken during the inspection. This can be determined based on the known optical imaging properties of the picture-taking device and the positions of the optical picture-taking device determined by the inspection path.

In a particularly advantageous embodiment of this method variation, points in time for taking the pictures are determined based on the displacement information of the displacement device and the determined picture-taking positions of the picture-taking device. By taking into account the actual displacement information of the displacement device and the picture-taking positions while the inspection path is being traveled, this information can be used directly in the optical scanning procedure in order to control or initiate picture-taking, particularly as a function of resolution, position and/or time.

According to the present invention, an illumination device can be assigned to the picture-taking device, and the inspection path is determined by specifying a specific geometric relationship between the picture-taking device, the illumination device, and the surface to be inspected. As a result, the inspection path is also determined with consideration for the illumination situation. For the case in which the illumination device and the picture-taking device are combined in a single inspection unit, the inspection path is determined for the inspection unit. It is also possible, however, to provide the picture-taking device and the illumination device with separate displacement devices, which can be moved independently of each other. In this case, the inspection path is specified such that a separate inspection path is specified for the picture-taking device and the illumination device, whereby the two inspection paths are coordinated with each other in terms of time. The same applies for the case in which several picture-taking devices, illumination devices and/or inspections units are provided.

The planning of the inspection path can include the planning of the motion sequences of all displacement devices and, optionally, of the object itself, if it is movable. To this end, in a particularly preferred variation of the present invention, a motion sequence for the relative motion between the object and the picture-taking device and/or the illumination device is determined from the inspection path.

In the determination of the motion sequence, it is preferably taken into account that the inspection time and/or inspection path be kept as short as possible in order to optimize the motion sequence during the inspection.

Since, depending on the optical picture-taking properties, e.g., camera focal length, the picture of the optical picture-taking device can have a much larger picture section than the area to be inspected on the surface, an inspection area within the picture can be assigned to each picture in the optical picture-taking device according to the present invention, the inspection area being evaluated during the inspection using image processing software.

To this end, it can be provided, in particular, that a check is carried out based on the inspection area and the inspection path to determine whether the object defined by the design data or the area to be inspected on the object are completely covered. This can take place, e.g., using a computer-aided simulation of the course of the inspection with reference to the calculated inspection paths, whereby the inspection areas defined in the pictures are marked on the object defined based on the design data, in order to check to determine whether all areas to be inspected have actually been covered.

To also make an additional manual control possible, it can be provided that the inspection path and/or the areas to be inspected on the defined object are visualized on a display means, particularly a screen.

The object according to the present invention is also attained via a method for determining areas to be inspected on a surface of a three-dimensional object based on electronically stored design data, particularly CAD data, relating to the object; this can be advantageously combined with the method described above. It is also possible, however, to apply the determination of areas to be inspected on an object separately from the planning of an inspection path. According to the present invention, it is specified for certain areas on the object whether and in what manner these areas are to be inspected; during the inspection with a picture-taking device, these areas to be inspected are then assigned to the pictures that were actually taken. As a result, a check is carried out during the inspection to determine whether all areas to be inspected were actually captured. This check carried out during the inspection can be used with automatic or manual path planning, and it ensures that the entire object was actually captured.

In a particularly advantageous embodiment of this inventive method, it is provided that areas not to be inspected, and/or areas to be inspected in a certain manner are determined automatically based on parameters capable of being determined from the design data related to the object, in particular geometric shapes or relationships. In this manner, all areas to be inspected on the object can also be determined automatically with reference to the design data. In contrast, the areas that cannot be inspected in a reasonable manner, e.g., due to their geometric shape, are automatically suppressed, without the need to manually select or label these areas. The manual effort required to select the areas to be inspected is thereby reduced considerably.

Preferably, the areas to be inspected can be stored as calculated or artificial pictures capable of being created using the design data on the object. These artificial pictures can then be compared with the pictures actually taken during the inspection. It is also possible to visualize these calculated pictures, in order to provide a possibility for performing an optical examination.

In a particular embodiment of this inventive method, the automatically generated areas to be inspected can be manually reworked, so that corrections can be made to the automatically generated inspection areas.

For control purposes, it can also be provided that the artificial pictures with the areas to be inspected and/or a visualization of the areas to be inspected are displayed in the pictures that were actually taken.

To more precisely assign the areas to be inspected to the actual pictures during the inspection, features in the areas to be inspected that are determined from the design data can be compared, according to the present invention, with the features that are recognizable in the pictures that were taken. If there is a deviation in the position of the features, this comparison can be used to perform a position correction by moving the features in the areas to be inspected and the pictures over one another. This lining-up simplifies the assignment of the areas to be inspected with the actual pictures for the further course of the inspection. In the search for features, pictures that have already been taken can be used in addition to the current picture.

According to particularly preferred embodiments of the two methods described above, the optical picture-taking devices are also calibrated three-dimensionally. This makes it possible to very exactly determine the position of the photographed object in the pictures themselves. This makes it possible to carry out fine-positioning based on the features recognizable in the pictures, which can be compared with the features in the design data. In this manner, it is therefore possible to perform a fine-positioning of the object by comparing the three-dimensionally calibrated data with the design data. This type of fine positioning is particularly advantageous, because it ensures that the areas to be inspected are projected correctly into the real pictures. This certainty does not exist when, e.g., only the position of the object to be inspected is detected very precisely using sensors, since further sources of error, e.g., the object sliding on the displacement device, are not reliably detected.

It is particularly advantageous when the picture-taking device and the displacement device are calibrated with respect to each other. Their coordinates relative to each other in a coordinate system are then known, so that their relative positions can be determined easily and exactly at any time.

Further features, advantages and possible applications of the inventive method are described in greater detail below with reference to exemplary embodiments and based on the drawing. All of the features described and/or depicted graphically are part of the present invention, either alone or in any combination and, in fact, independently of their wording in the claims or their back-references.

Figure 1:
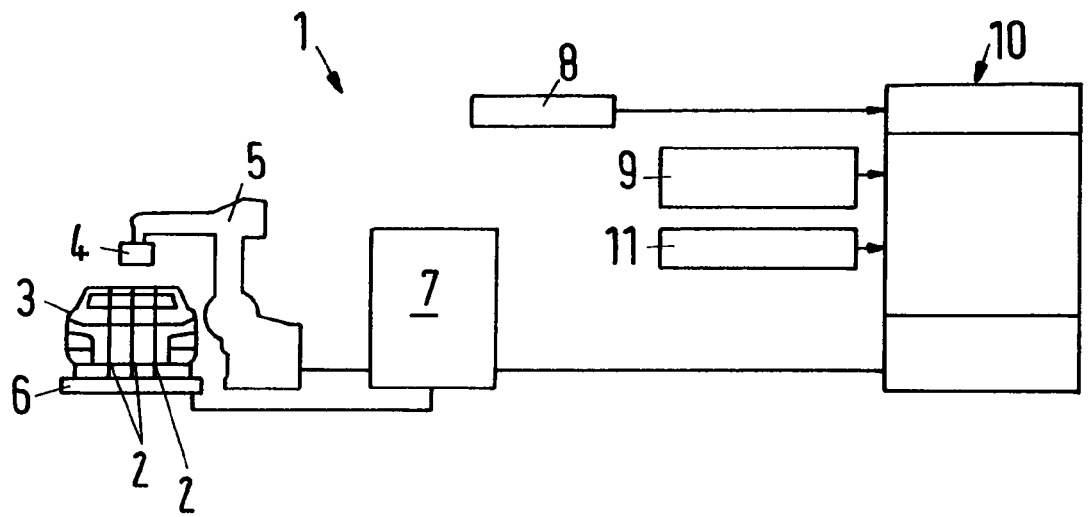
FIG. 1 is a schematic illustration of the sequence for planning an inspection path.
Figure 2:
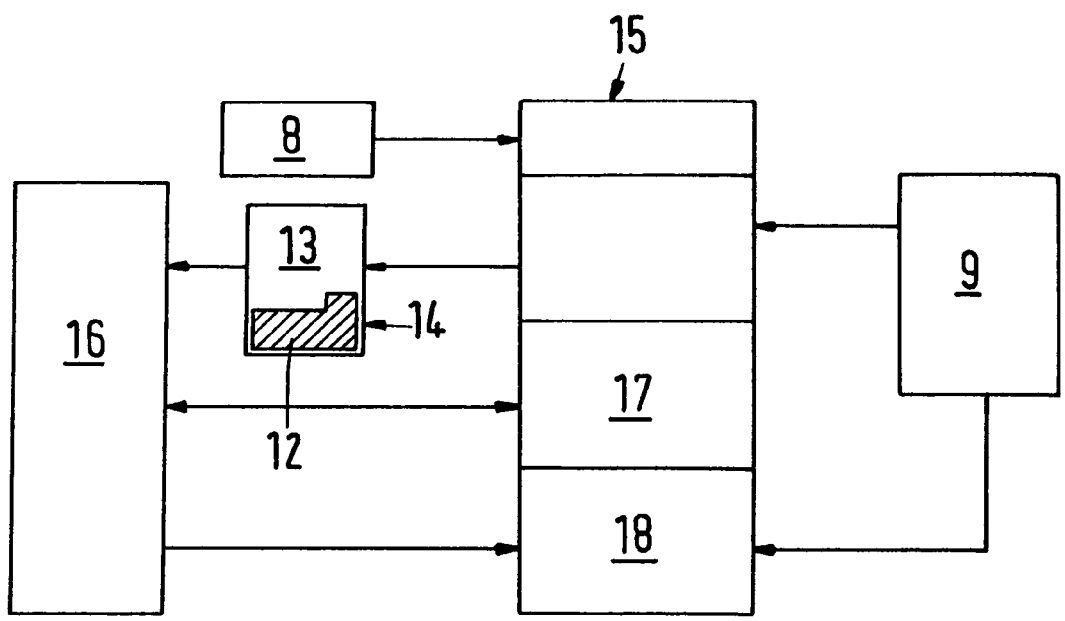
FIG. 2 is a schematic illustration of the sequence for determining areas to be inspected on a surface.

FIG. 1 is a schematic illustration of a system 1 for inspecting a surface, with which, according to the inventive method, inspection paths 2 are determined over a three-dimensional object 3—shown as a body—for an optical picture-taking device 4. This system is suited for use in paint inspections, for example. It is not limited to use in paint or surface inspections of bodies, however. The advantage of this lies in the fact that this system can be used in a flexible manner for highly diverse applications, and it can be easily reconfigured.

In the example shown, optical picture-taking device 4 is integrated in an inspection unit in which at least one camera—as the picture-taking device 4—and at least one illumination device are located. Optical picture-taking device 4 can be moved using a displacement device 5 designed as a robot or a manipulator relative to three-dimensional object 3, which is movable over a displacement device 6 designed as a conveyor belt. As a result, a relative motion between optical picture-taking device 4 and three-dimensional object 3 can be attained. Displacement devices 5 and 6 are controlled by a common control device 7.

Electronically-stored design data 8 are available on object 3 and/or areas to be inspected on object 3, design data 8 being CAD data of a corresponding three-dimensional design program in particular. The three-dimensional design of object 3 can be derived from these design data. Furthermore, the optical imaging properties of picture-taking device 4 are known as camera parameters 9. These camera parameters 9 are preferably created using automatic camera calibration that includes the imaging properties and the position of optical picture-taking device 4 or the camera in space.

Calibrations of this type can be carried out automatically based on plates with patterns, e.g., points, located in fixed, known positions. Based on the known positions and patterns of the calibration plates, the imaging properties of cameras 4 and their position in space are determined very accurately. When a camera is used that is installed in a fixed position, with which the relative motion between three-dimensional object 3 and the stationary camera takes place via displacement device 6 assigned to object 3, the calibration plate can be located on a separate displacement device. To carry out the calibration, the displacement devices with optical picture-taking device 4 and/or the calibration plate can be moved into a calibration position, a picture can be taken, and it can be evaluated using the appropriate calibration software.

Design data 8 and camera parameters 9 are read in by an arithmetic logic unit 10. With these data, arithmetic logic unit 10 can automatically determine—in accordance with the inventive method—inspection path(s) 2 for the optical picture-taking device 4 by specifying a specific geometric relationship between the picture-taking device and the surface to be inspected. By specifying the geometric relationship, e.g., the distance between the surface to be inspected and optical picture-taking device 4 and/or the angle between the surface normals and the optical axis of picture-taking device 4, a program of arithmetic logic unit 10 can calculate—with reference to electronic design data 8 and camera parameters 9—optical inspection path 2 of optical picture-taking device 4 for object 3. Support points to be connected with each other via an inspection path 2 can also be specified in design data 8.

In the case of a system with a stationary picture-taking device, possible inspection paths 2 are predefined depending on the orientation of the picture-taking device. In this case, the planning of inspection path 2 is limited to calculating the image track followed by the optical picture-taking device over body 3. With movable picture-taking devices 4, on the other hand, the position of the picture-taking device can be adapted in a flexible manner to the surface shape of object 3 to be examined. With smaller optical picture-taking devices 4 in particular, it is possible to plan the inspection path over the surface of object 3 in a freely defined manner, since optical picture-taking device 4 can be guided over stationary or moving object 3 with a large number of degrees of freedom.

When planning inspection path 2, the particular picture-taking positions are determined by using the known optical picture-taking properties such that entire three-dimensional object 3 or all previously-specified areas to be inspected on object 3 are covered by the pictures that were taken. Entire inspection path 2 can also be composed of several, non-connected path sections that are connected via intermediate paths. The intermediate paths are covered at a high rate of speed, since no pictures are taken on these intermediate paths.

Based on inspection path 2 for optical picture-taking device 4 and using displacement information 11 that includes the possible displacements of displacement device 5, 6, a motion sequence for the relative motion between object 3 and picture-taking device 4 can be determined. This motion sequence is output by arithmetic logic unit 10 to control device 7, which controls displacement devices 5, 6. Finally, with consideration for displacement information 11 of displacement device 5, 6 and the previously determined picture-taking positions of picture-taking device 4, the correct points in time for taking pictures during the motion sequence of displacement devices 5, 6 can be determined.

With the planning of inspection path 2 according to the present invention, all paths are therefore determined that individual picture-taking devices 4 and cameras must follow over object 3, e.g., the body, so that pictures are taken of all areas to be inspected on the object. Based on these inspection paths 2, the motion sequence of various displacement devices 5, 6 is then determined, e.g., in the form of manipulator paths to be traveled. The points in time for taking pictures by particular optical picture-taking device 4 are determined along these manipulator paths based on the predetermined picture-taking positions on the inspection path by, e.g., specifying the camera positions associated with the particular points in time. This motion sequence is supplied by arithmetic logic unit 10, as a control program, to control device 7, which then automatically moves displacement devices 5, 6 into the correct positions.

In addition to the automatic path planning, the present invention also provides a method for determining areas 12 to be inspected on a surface. Often there are zones on three-dimensional object 3, e.g., a body, that are not to be inspected. They can be, e.g., painted surfaces, which will be subsequently covered with molding strips or protective molding rails, window pane folds, bending folds of beading, lateral surfaces of concave indentations, such as license plate indentations, sheet-metal edges, or the like.

Figure 3:
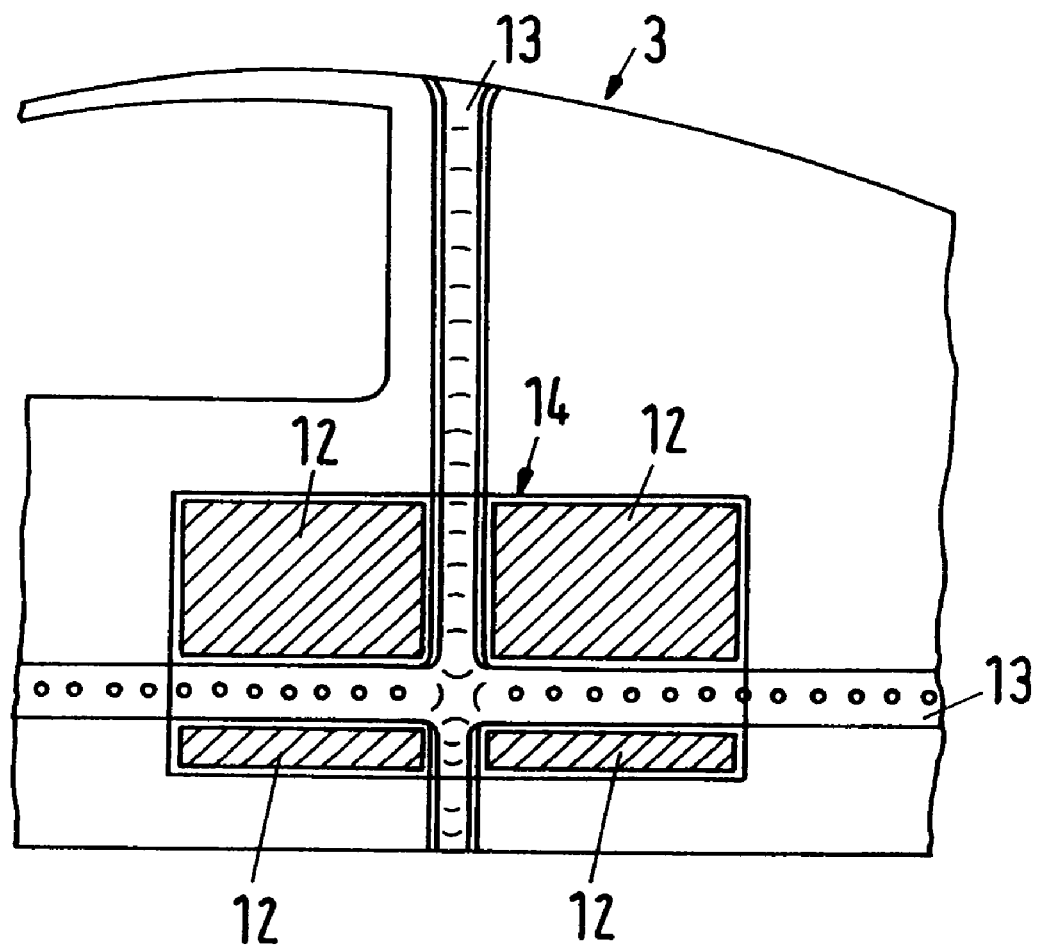
FIG. 3 is a schematic illustration of a picture with areas to be inspected on an object.

Areas 13 of this type that are not to be inspected are shown in FIG. 3. They involve a vertical pillar and a horizontal attachment surface for a protective strip on a body 3. Areas 13 not to be inspected can be determined automatically from design data 8 based on their geometric shape and their appearance. These areas 13 not to be inspected are specified on object 3. The same applies for areas 12 to be inspected, and, in fact, these areas 12 to be inspected are assigned to the pictures that were actually taken while the inspection was being carried out with an picture-taking device 4. The assignment to the pictures can take place based on design data 8 and known camera parameters 9, so that a picture 14 from an optical picture-taking device 4 includes areas 12 to be inspected and areas 13 not to be inspected.

These areas 12, 13 are determined using an arithmetic logic unit 15 based on design data 8 and camera parameters 9 of optical picture-taking device 4 that contain the optical imaging properties and the camera positions. Arithmetic logic unit 15 can be identical to arithmetic logic unit 10 used to automatically plan the path. Arithmetic logic unit 15 calculates all pictures to be taken by the camera during the inspection and depicts areas 12 to be inspected in them. Areas 13 not to be inspected are the complements thereof in calculated pictures 14.

The automatically generated areas 12 to be inspected in calculated pictures 14 can be reworked, e.g., with a graphic fine editor 17. Various inspection zones can also be specified using fine editor 17.

Pictures 14—created by arithmetic logic unit 15 and possibly reworked by fine editor 17—with areas 12 to be inspected and/or areas 13 not to be inspected are stored for each picture-taking device 4 in a memory 16. The reworking is carried out using graphic editor 17 contained in arithmetic logic unit 15.

To check whether areas 12 to be inspected and that are stored in memory device 16 for each camera actually cover the entire desired surface, a checking module 18 is provided in arithmetic logic unit 15 that checks the coverage of object 3 with areas 12 to be inspected.

To obtain an accurate orientation of object 3 in the pictures actually taken by the camera in conformance with calculated camera pictures 14 in which areas 12, 13 to be inspected and/or not to be inspected, respectively, are defined, a fine-positioning of object 13 is carried out by comparing the three-dimensionally calibrated pictures that were taken with design data 8. This ensures that calculated pictures 14 and the pictures taken by the camera are truly accurately superimposed. This can be accomplished by examining pronounced geometric shapes in pictures 14 calculated based on design data 8 and the pictures that were taken. This ensures that, in particular, areas 12 to be inspected are defined correctly in the pictures that were taken, and that they are processed correctly in the subsequent image evaluation.

By way of the automatic path planning and determination of areas to be inspected, which takes place automatically, in particular, based on the design data and which is checked while the inspection is being carried out, the surface inspection is greatly simplified using optical picture-taking systems, since manual configuration of the inspection system and manual specification of inspection paths are largely eliminated.

REFERENCE NUMERALS

1 System for inspecting surfaces
2 Inspection path
3 Three-dimensional object, body
4 Optical picture-taking device
5 Displacement device, manipulator
6 Displacement device, conveyor belt
7 Control unit
8 Design data
9 Camera parameters, optical imaging properties
10 Arithmetic logic unit
11 Displacement information
12 Areas to be inspected
13 Areas not to be inspected
14 Pictures
15 Arithmetic logic unit
16 Memory
17 Fine editor
18 Checking module

What is claimed is:

1. A method of planning an inspection path for at least one optical picture-taking device for inspecting a three-dimensional object, wherein the at least one picture-taking device and the object are movable relative to each other using at least one displacement device, said method comprising:
    a) assigning at least one illumination device to said at least one optical picture-taking device;
    b) automatically determining at least one area on said surface of said three-dimensional object to be inspected, at least one other area on said surface of said three-dimensional object that is not to be inspected, and a respective manner in which said at least one area is to be inspected with an arithmetic logic unit based on design data in electronic form related to said three-dimensional object;
    c) planning an inspection path for said at least one optical picture-taking device for inspection of said three-dimensional object based on said at least one area to be inspected on said surface of said three-dimensional object determined in step b, based on said design data, and based on optical imaging characteristics of said at least one optical picture-taking device, stored in an electronic form;
    d) automatically determining said inspection path for said at least one optical picture-taking device by specifying a predetermined geometric relationship between said at least one optical picture-taking device, said at least one illumination device, and said surface on said three-dimensional object to be inspected by using said arithmetic logic unit so that said inspection path or an inspection time is as short as possible;
    e) determining a motion sequence for relative motion between said three-dimensional object and said at least one optical picture-taking device or said illumination device for the at least one optical picture-taking device from said inspection path; and
    f) assigning said at least one area on said surface of said three-dimensional object to be inspected to pictures that were actually taken with said at least one optical picture-taking device during an inspection with said optical picture-taking device.

2. The method according to claim 1, wherein said design data is CAD data or is determined by a sensor.

3. The method according to claim 1, wherein said at least one area on said surface of said three-dimensional object to be inspected is electronically stored or visualized as a calculated picture.

4. The method according to claim 3, wherein said at least one area on said surface of said three-dimensional object to be inspected in said respective manner automatically based on said design data is capable of being processed manually.

5. The method according to claim 4, further comprising displaying said calculated picture of said at least one area on said surface of said three-dimensional object to be inspected in said pictures that were actually taken during said inspection.

6. The method according to claim 5, further comprising automatically comparing features in said at least one area on said surface of said three-dimensional object to be inspected in said respective manner based on said design data with features recognizable in said pictures that were actually taken during said inspection, and then carrying out a position correction, if necessary, based on results of the comparing.

7. The method according to claim 6, further comprising three-dimensionally calibrating said optical picture-taking device.

8. The method according to claim 7, further comprising a fine-positioning of said three-dimensional object in said pictures that were actually taken.

9. The method according to claim 1, further comprising determining picture-taking positions of the optical picture-taking device so as to cover said three-dimensional object or said at least one area on said surface of said three-dimensional object to be inspected with said pictures that were actually taken during said inspection.

10. The method according to claim 9, wherein points in time for taking said pictures are determined considering displacement information of said displacement device and said picture-taking positions of said optical picture-taking device.

11. The method according to claim 1, further comprising performing a check, based on said at least one area on said surface of said three-dimensional object to be inspected and said inspection path, to determine whether said three-dimensional object defined by said design data or an entire area of said surface to be inspected on said three-dimensional object defined by said design data, has been completely covered.

12. The method according to claim 1, further comprising visualizing said inspection path or said at least one area defined on said surface of said three-dimensional object to be inspected on display means.

13. The method according to claim 12, wherein said display means is a display device.

* * * * *